(12) United States Patent
Comins et al.

(10) Patent No.: US 7,132,545 B2
(45) Date of Patent: Nov. 7, 2006

(54) SYNTHESIS OF NICOTINE DERIVATIVES FROM NICOTINE

(75) Inventors: Daniel L. Comins, Cary, NC (US); Emilie Despagnet Smith, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 11/254,895

(22) Filed: Oct. 20, 2005

(65) Prior Publication Data

US 2006/0041135 A1   Feb. 23, 2006

Related U.S. Application Data

(62) Division of application No. 10/925,516, filed on Aug. 25, 2004, now Pat. No. 6,995,265.

(60) Provisional application No. 60/497,826, filed on Aug. 26, 2003.

(51) Int. Cl.
C07D 401/04   (2006.01)
C07D 401/02   (2006.01)
(52) U.S. Cl. ................. 546/276.4; 546/279.4
(58) Field of Classification Search ............ 546/276.4, 546/279.4
See application file for complete search history.

(56) References Cited

U.S. PATENT DOCUMENTS 5,594,011 A   1/1997   McDonald et al.
5,723,477 A   3/1998   McDonald et al.

OTHER PUBLICATIONS

Bleicher, et al. A Practical and Efficient Synthesis of the Selective Neuronal Acetylcholine-Gated Ion Channel Agonist (S)-(-)-5-Ethynyl-3-(1-methyl-2-pyrrolidinyl)pyridine Maleate (SIB-1508Y). *J. Org. Chem.* 63: 1009-1118 (1998).
Brown, et al. A Convenient Synthesis of Dimethyl (Diazomethyl)phosphate (Seyferth/Gilbert Reagent). *J. Org. Chem.* 61:2540-2541 (1996).
Kondo, et al. TMP-Zincate as Highly Chemoselective Base for Directed Ortho Methylation. *J. Am. Chem. Soc.* 121:3539-3540 (1999).

*Primary Examiner*—Charanjit S. Aulakh
(74) *Attorney, Agent, or Firm*—Myers Bigel Sibley & Sajovec

(57) ABSTRACT

Methods of synthesizing nicotine analogs and derivatives are described. In some embodiments the methods utilize an alkyl or aryl silyl-substituted nicotine analog intermediate. Intermediates useful for the synthesis of nicotine and nicotine analogs are also described.

5 Claims, No Drawings

SYNTHESIS OF NICOTINE DERIVATIVES FROM NICOTINE

CLAIM FOR PRIORITY AND CROSS-REFERENCE TO OTHER APPLICATIONS

This application claims priority to and is a divisional of parent application Ser. No. 10/925,516, filed on Aug. 25, 2004, now U.S. Pat. No. 6,995,265, which claims the benefit of U.S. Provisional Application Ser. No. 60/497,826, filed Aug. 26, 2003, the disclosures of which are incorporated herein by referenced in their entirety.

FIELD OF THE INVENTION

The present invention concerns methods and intermediates useful for the synthesis of compounds active for modulating nicotinic acetylcholine receptors.

BACKGROUND OF THE INVENTION

Acetylcholine receptors are involved in the modulation of of a variety of physiological and behavioral finctions, including neuroendocrine function, respiration, mood, motor control and function, focus and attention, concentration, memory and cognition, and substance abuse. Ligands for acetylcholine receptors have been demonstrated to have effects on attention, cognition, appetite, substance abuse, memory, extrapyramidal function, cardiovascular function, pain and gastrointestinal motility and function. The distribution of acetylcholine receptors that bind nicotine, i.e., nicotinic acetylcholine receptors, is widespread in the brain. In the periphery, acetylcholine receptors are found in muscle, autonomic ganglia, the gastrointestinal tract and the cardiovascular system (see, e.g., U.S. Pat. No. 5,594,011).

Acetylcholine receptors have been shown to be decreased, among other things, in the brains of patients suffering from Alzheimer's disease, and Parkinson's disease, as well as diseases associated with dementia, motor dysfunction and cognitive impairment. Such correlations between acetylcholine receptors and nervous system disorders suggest that compounds that modulate acetylcholine receptors will have beneficial therapeutic effects for many human nervous system disorders. U.S. Pat. No. 5,594,011 to McDonald et al., assigned to SIBIA Neuroscience, describes compounds such as SIB-1508Y that modulate nicotinic acetylcholine receptors. Such compounds are useful for, among other things, the treatment of Parkinson's disease. See also U.S. Pat. No. 5,723,477 to McDonald et al. Unfortunately, nicotine analogs are difficult compounds to synthesize, and there is a continuing need for new methods of making the same, as well as intermediates useful for the synthesis of nicotine analogs.

SUMMARY OF THE INVENTION

A first aspect of the present invention is a method of making a compound of Formula i:

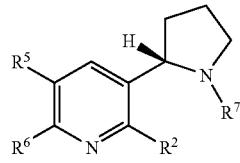

wherein:

$R^2$, $R^5$, and $R^6$ are each independently selected from the group consisting of H, alkyl, aryl, alkenyl, alkynyl, alkoxy, and halo, preferably H or alkyl (e.g. methyl);

$R^7$ is selected from the group consisting of consisting of H and alkyl (e.g., methyl); and $R^{20}$, $R^{21}$ and $R^{22}$ are each independently selected from the group consisting of alkyl and aryl, preferably alkyl such as methyl. The method comprises:

reacting a compound of the formula:

with lithium and a compound of the formula $XSiR^{20}R^{21}R^{22}$, where X is halo, in a polar aprotic solvent to produce the compound of Formula i.

A second aspect of the present invention is a method of making a compound of Formula ii:

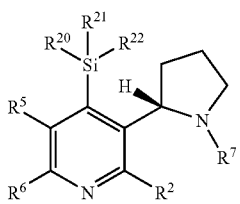

wherein $R^2$, $R^5$, and $R^6$ are as given above, $R^7$ is as given above, and $R^{20}$, $R^{21}$ and $R^{22}$ are given above. The method comprises oxidizing a compound of Formula i as given above to produce the compound of Formula ii.

A third aspect of the present invention is a method of making a compound of Formula iii:

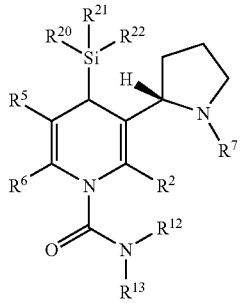

iii wherein $R^2$, $R^5$, and $R^6$ are as given above, $R^7$ is as given above, $R^{12}$ and $R^{13}$ are each independently selected from the group consisting of H, alkyl and aryl, preferably H or alkyl (e.g., methyl), and $R^{20}$, $R^{21}$ and $R^{22}$ are as given above. The method comprises reacting a compound of Formula i as given above with a compound of the formula:

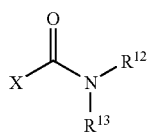

where X is halo such as chloro in a polar aprotic solvent to produce the compound of Formula iii.

A fourth aspect of the present invention is a method of making a compound of Formula iv:

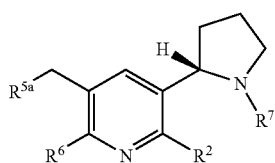

iv wherein $R^2$ and $R^6$ are as given above, $R^{5a}$ is ary, such as phenyl; and $R^7$ is as given above. The method comprises reacting a compound of formula i as given above, wherein wherein $R^5$ is H, and $R^{20}$, $R^{21}$ and $R^{22}$ are as given above, with a compound of the formula:

in a polar organic solvent containing fluoride to produce the compound of Formula iv.

A further aspect of the present invention is a method of making a compound of Formula VI:

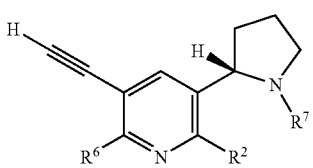

VI wherein $R^2$ and $R^6$ are each independently selected from the group consisting of H, alkyl, aryl, alkenyl, alkynyl, alkoxy, and halo (preferably H or alkyl such as methyl), and $R^7$ is selected from the group consisting of consisting of H and alkyl (preferably methyl). The method comprises reacting a compound of Formula V:

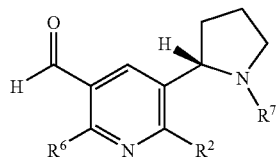

V with a compound of formula:

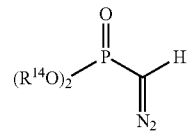

where $R^{14}$ is alkyl (such as methyl) to produce the compound of Formula VI:

A further aspect of the present invention is a method of making a compound of Formula V as given above. The method comprises reacting a compound of Formula IV:

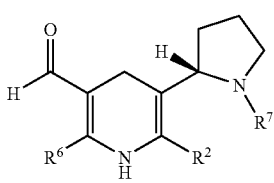

IV where $R^2$, $R^6$ and $R^7$ are as given above with sulfur to produce the compound of Formula V.

A further aspect of the present invention is a method of making a compound of Formula IV as given above. The method comprises reacting a compound of Formula III:

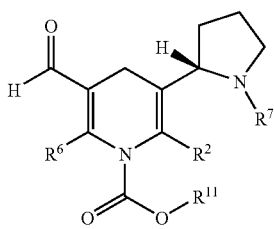

III wherein $R^2$, $R^6$ and $R^7$ are as given above and $R^{11}$ is alkyl or aryl, preferably alkyl, with a base to produce the compound of Formula IV.

A further aspect of the present invention is a method of making a compound of Formula III as given above. The method comprises reacting a compound of Formula II:

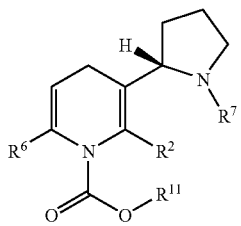

wherein $R^2$, $R^6$, $R^7$, and $R^{11}$ are as given above, with a compound of the formula $POX_3$, where X is halo, and a formamide to produce the compound of Formula III.

A further aspect of the present invention is a method of producing a compound of Formula II as given above. The method comprises reacting a compound of Formula I:

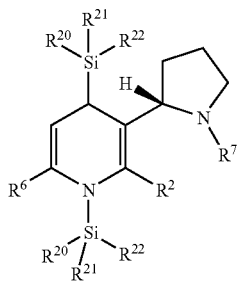

wherein $R^2$, $R^6$, $R^7$, $R^{20}$, $R^{21}$ and $R^{22}$ are as given above (note compounds of Formulas i and Formulas I are the same herein) with a compound of the formula:

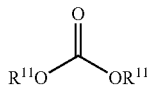

where $R^{11}$ is as given above to produce the compound of Formula II.

A further aspect of the present invention is compounds of Formulas i, ii, iii and iv above, and compounds of Formulas I, II, III, IV and V above, which compounds are useful, among other things, as compounds having nicotinic acetylcholine receptor modulating activity, and as intermediates for making compounds having nicotinic acetylcholine receptor modulating activity, all as described in greater detail below.

The foregoing and other objects and aspects of the present invention are explained in greater detail below.

DETAILED DESCRIPTION OF THE PREFERRED EMBODIMENTS

"Alkyl" as used herein refers to straight or branched chain alkyl groups having in the range of about 1 up to 12 carbon atoms. "Lower alkyl" refers to straight or branched chain alkyl radicals having in the range of about 1 up to 4 carbon atoms. Alkyl and loweralkyl may be substituted or unsubstituted unless specified otherwise herein; "substituted alkyl" refers to alkyl, cycloalkyl or lower alkyl groups further bearing one or more substituents such as hydroxy, alkoxy (of a lower alkyl group), aryl, mercapto (of a lower alkyl group), halogen, trifluoromethyl, cyano, nitro, amino, carboxyl, carbamate, sulfonyl, sulfonamide, and the like. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, cyclohexyl, and the like.

"Alkoxy" as used herein refers to a compound of the formula RO—, where R is alkyl or loweralkyl (which may be substituted or unsubstitued unless specified otherwise) as given above.

"Alkenyl" refers to straight or branched chain hydrocarbyl groups such as alkyl or loweralkyl groups as described above (and which may be substituted or unsubstituted unless specified otherwise) and having at least one carbon-carbon double bond.

"Alkynyl" refers to straight or branched chain hydrocarbyl groups such as alkyl or loweralkyl groups as described above (and which may be substituted or unsubstituted unless specified otherwise) and having at least one carbon-carbon triple bond.

"Aryl," as used herein, refers to a monocyclic carbocyclic ring system or a bicyclic carbocyclic fused ring system having one or more aromatic rings. Examples of aryl include but are not limited to azulenyl, indanyl, indenyl, naphthyl, phenyl, tetrahydronaphthyl, and the like. The aryl groups may be substituted or unsubstituted unless specified otherwise and when substituted can for example be substituted with 1, 2, 3, 4, or 5 substituents independently selected from alkyl, alkenyl, alkenyloxy, alkoxy, alkoxyalkoxy, alkoxycarbonyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, —NR'R" (wherein R' and R" are independently selected from hydrogen, alkyl, alkylcarbonyl, aryl, arylalkyl and formyl), and —C(O)NR'R" (wherein R' and R" are independently selected from hydrogen, alkyl, alkylcarbonyl, aryl, arylalkyl, and formyl).

"Halo" refers to fluoro, chloro, bromo or iodos.

The disclosures of all United States patent references cited herein are to be incorporated herein by reference in their entirety.

In a first aspect, the present invention provides a set of reactions for the synthesis of derivatives from nicotine and nicotine analogs. This set of reactions is referred to with reference to compounds of Formulas i–iv herein. Thus in one respect the present invention provides a method of making a compound of Formula i:

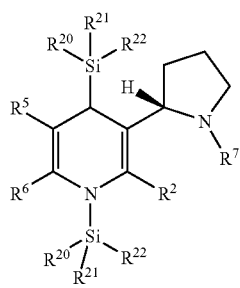

wherein $R^2$, $R^5$, and $R^6$ are each independently selected from the group consisting of H, alkyl, aryl, alkenyl, alkynyl, alkoxy, and halo (preferably H and alkyl, most preferably H), $R^7$ is selected from the group consisting of consisting of H and alkyl (preferably alkyl, most preferably methyl), and $R^{20}$, $R^{21}$, and $R^{22}$ are alkyl or aryl (preferably alkyl, most preferably methyl). Compounds that may be used as starting materials for the reactions described herein (including the preparation of compounds of Formula i) include both nicotine and nicotine analogs and derivatives, particularly analogs substituted at the 2 and 6 position, including but not limited to those described in U.S. Pat. Nos. 5,594,011 and 5,723,477. The method comprises reacting a precursor nicotine or nicotine analog such as compounds of the formula:

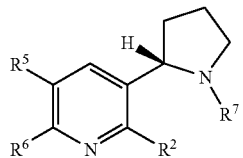

(which precursor nicotine or nicotine analog may be produced in accordance with known techniques as noted above) with lithium (e.g., lithium powder) and a compound of the formula $XSiR^{20}R^{21}R^{22}$ where X is halo preferably chloro (and the compound is preferably trialkylchlorosilane, most preferably trimethylchlorosilane) in a polar aprotic solvent (such as tetrahydrofuran) to produce the compound of Formula i. The method may be carried out for any suitable time and temperature, such as −20° C. to 25° C. or more, and is preferably carried out at a temperature of about 0° C.

A further aspect of the present invention is a method of making a compound of Formula ii:

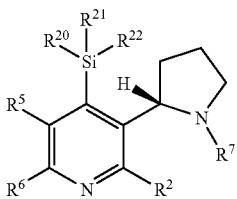

wherein $R^2$, $R^5$, and $R^6$, $R^7$, $R^{20}$, $R^{21}$ and $R^{22}$ are as given above. The method comprises oxidizing a compound of Formula i as described above to produce the compound of Formula ii. The method may be carried out with any suitable oxidizing agent, preferably air. Compounds of Formula ii are useful as insecticides for insects such as mosquitos and are useful as intermediates for making nicotine and nicotine analogs.

The present invention further provides a method of making a compound of Formula iii:

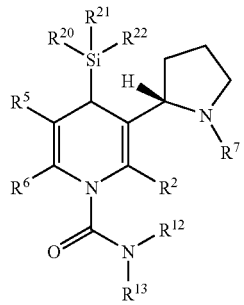

wherein $R^2$, $R^5$, $R^6$, $R^7$, $R^{20}$, $R^{21}$ and $R^{22}$ are as described above, and $R^{12}$ and $R^{13}$ are each independently selected from the group consisting of H, alkyl, and aryl (preferably alkyl, most preferably methyl). In general, the method comprises reacting a compound of Formula i as described above with a compound of the formula

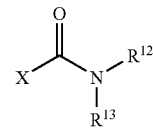

where X is halo, preferably chloro. The reaction may be carried out in a polar aprotic solvent, preferably methylene chloride, at any suitable temperature, typically from 0° C. to 100° C., and preferably at room temperature.

The present invention further provides a method of making a compound of Formula iv:

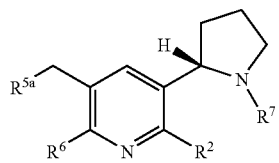

wherein $R^{5a}$ is substituted or unsubstituted aryl, and $R^2$, $R^6$ and $R^7$ are as given above. The method comprises reacting a compound of formula i, wherein $R^5$ is H, with a compound of the formula:

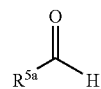

in a polar organic solvent such as tetrahydrofuran containing fluoride (preferably by addition of a fluoride source such as TBAF) to produce said compound of Formula iv.

Reactions for the synthesis of compounds such as SIB-1508Y. In another respect, the present invention provides methods for the synthesis of compounds having acetylcholine receptor modulating activity including pharmaceutical compounds or insecticides from nicotine and nicotine analogs. These methods are referred to with respect to compounds of Formulas I–VI herein. In one aspect, such methods involve methods of making compounds of Formula II:

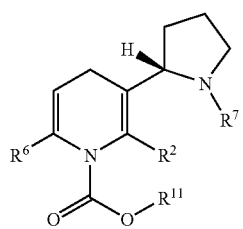

II wherein $R^{11}$ is alkyl or aryl (preferably alkyl, most preferably methyl), and $R^2$, $R^6$, and $R^7$ are as given above. Such compounds may be made by reacting a compound of Formula i above (in this section referred to as Formula I):

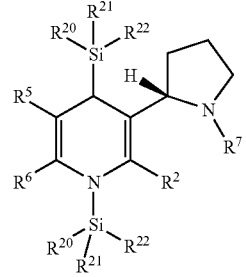

I with a compound of the formula:

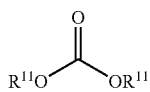

(wherein $R^{11}$ is as given above) in a polar aprotic solvent such as tetrahydrofuran containing fluoride (e.g., by addition of tetrabutylammonium fluoride or other appropriate fluoride source) to produce the compound of Formula II. The reaction may be carried out at any suitable temperature, for example from 10 to 50 or 75° C., preferably room temperature.

A further aspect of the invention is a method of making compounds of Formula III:

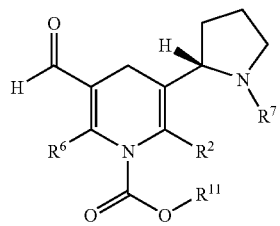

III wherein $R^2$, $R^6$, $R^7$ and $R^{11}$ is as given above. Such compounds may be produced by reacting a compound of Formula II as described above with $POX_3$ where X is halo, preferably chloro, and a formamide (preferably a dialkyl formamide and most preferably dimethylformamide) in a polar aprotic solvent such as methylene chloride, chloroform, carbon tetrachloride or the like to produce said compound of Formula III. The reaction may be carried out at any suitable temperature, typically between room temperature and 100° C.

A further aspect of the present invention is a method of making compounds of Formula IV:

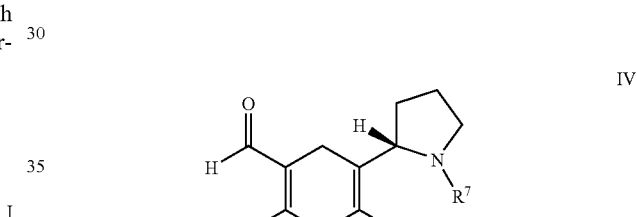

IV wherein $R^2$, $R^6$ and $R^7$ are as given above. Such methods generally involve reacting a compound of Formula III as described above with a a base, preferably a mild base such as triethylamine, an alkoxide or methoxide such as sodium, lithium or potassium alkoxide or methoxide, in a polar organic solvent (e.g., methanol, ethanol, propanol) to produce the compound of Formula IV. The reaction can be carried out under any suitable conditions, typically from 0 to 100° C., preferably at room temperature.

The present invention provides methods of making compounds of Formula V:

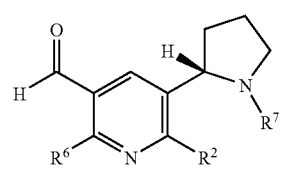

V (wherein $R^2$, $R^6$ and $R^7$ are as given above) by reacting a compound of Formula IV as described above with sulfur (e.g., elemental sulfur) in a polar or nonpolar organic solvent (e.g., toluene, benzene, higher molecular weight non-polar solvents, alcohols) to produce the compound of Formula V. Such reactions may be carried out under any suitable conditions, preferably by reflux, for any suitable time (e.g., 1–24 hours).

Finally, the present invention provides methods of making compounds of Formula VI:

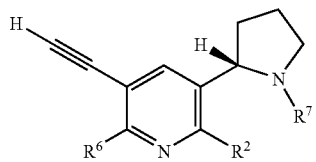

wherein $R^2$, $R^6$ and $R^7$ are as given above. The methods comprise reacting a compound of Formula V as described above with a compound of formula:

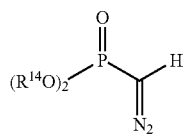

wherein $R^{14}$ is alkyl, preferably methyl, in the presence of a strong base (i.e., potassium tert-butoxide) in a polar aprotic solvent such as tetrahydrofuran to produce the compound of Formula VI.

Compounds of Formula VI are useful in the manners described in U.S. Pat. No. 5,594,011 to McDonald et al. and U.S. Pat. No. 5,723,477 to McDonald et al., and compounds of Formulas I–V are useful as intermediates for making the same.

In summary, methods and intermediates of the present invention are useful for producing pharmacologically and pharmaceutically active compounds, including compounds useful for the treatment of neurological disorders such as Parkinson's disease, Alzheimer's disease, motor dynsfunction and cognitive impairment in human and animal subjects, as well as compounds for use as an alternative to nicotine as an aid to smoking cessation programs, as insecticides, etc.

The present invention is explained in greater detail in the following non-limiting Examples.

EXAMPLES 1–3

Preparation of Enantiopure Nicotine Derivatives i–iv

Scheme 1

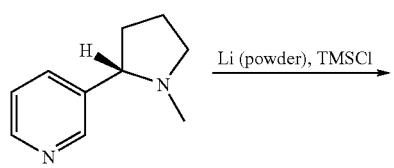

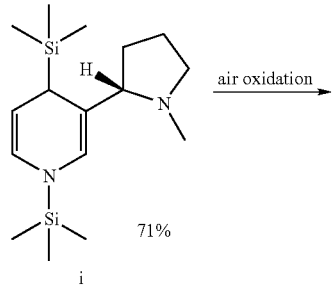

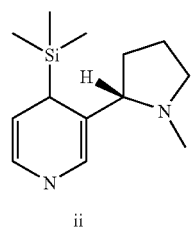

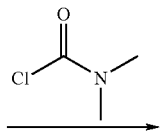

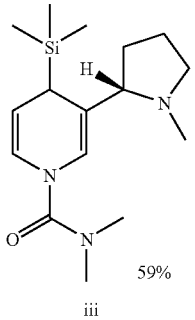

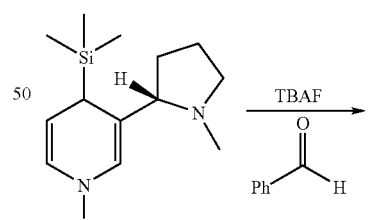

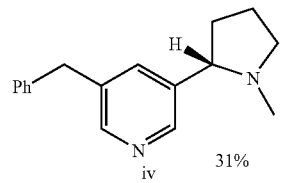

EXAMPLES 1–2

Preparation of (S)-3-(1-Methylpyrrolidin-2-yl)-1,4-bis-trimethylsilanyl-1,4-dihydro-pyridine (i) and (S)-3-(1-Methylpyrrolidin-2-yl)-4-trimethylsilanylpyridine (ii)

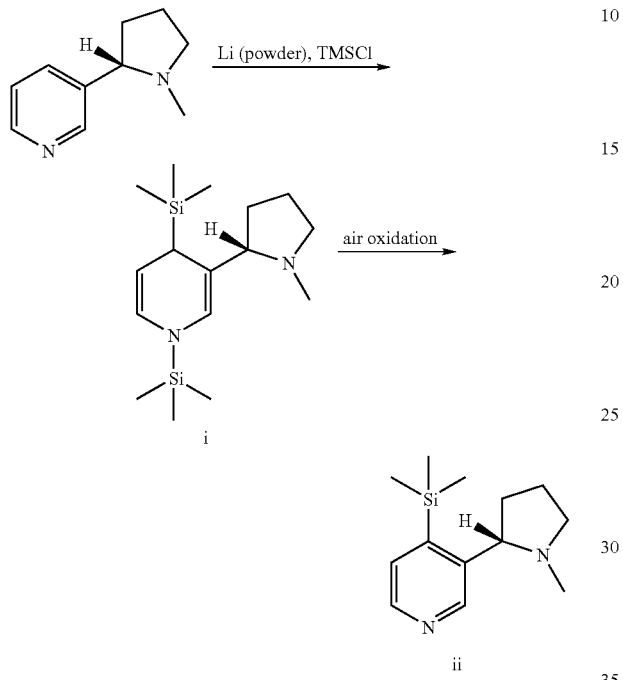

To a suspension of lithium powder (0.42 g, 60 mmol) in freshly distilled THF (20 mmol) cooled at −10° C. was added freshly distilled trimethylchlorosilane (7.6 mL, 60 mmol). A solution of (S)-nicotine (3.2 mL, 20 mmol) in THF (20 mL) was injected dropwise over 20 min. The reaction mixture was stirred at 0° C. for 1 h. The precipitate formed was decanted over 2 h and the liquid portion was canulated into a 2 neck flask mounted with a distillation apparatus under Ar. After removal of the THF by distillation at atmospheric pressure, the product was distilled under vacuum (1.5 mm Hg, bp=130–135° C.) to give 71% (4.36 g) of 3-(1-methylpyrrolidin-2-yl)-1,4-bis-trimethylsilanyl-1,4-dihydropyridine i as a yellow oil (95% pure by NMR). $^1$H NMR (400 MHz, CDCl$_3$): δ 8.24 (s, 1 H), 5.78–5.72 (m, 1 H), 4.37–4.29 (m, 1 H), 3.06–2.93 (m, 1 H), 2.4–1.4 (m, 10 H), 0.08 (s, 9 H), −0.05 (s, 9 H). $^{13}$C NMR (100 MHz, CDCl$_3$) δ 127.49, 126.41, 121.14, 102.08, 101.00, 66.67, 57.21, 41.05, 32.52, 26.41, 21.84, −0.83, −0.90, −2.43, −2.64. HRMS Calcd for C$_{16}$H$_{32}$N$_2$Si$_2$: 309.2182 [M+H]$^+$. Found: 309.2166 [M+H]$^+$.

3-(1-Methylpyrrolidin-2-yl)-1,4-bis-trimethylsilanyl-1,4-dihydropyridine i is easily converted to 3-(1-methylpyrrolidin-2-yl)-4-trimethylsilanylpyridine ii when in contact with air. Compound ii can be purified by RPLC (silica gel, 5% EtOAc/hex) to give a clear oil. IR (thin film, neat, NaCl): 2955, 2768, 1338, 1243, 1844 cm$^{-1}$; $^1$H NMR (400 MHz, CDCl$_3$): δ 8.86 (s, 1 H), 8.42 (d, 1 H, J=6.4 Hz), 7.28 (dd, 1 H, J=1.2 and 6.8 Hz), 3.36–3.24(m, 2 H) 2.35–1.60 (m, 8 H), 0.37 (s, 9 H); $^{13}$C NMR (100 MHz, CDC$_3$) δ 149.16, 147.64, 147.01, 127.88, 68.89, 56.94, 40.45, 36.50, 22.82, 0.51. HRMS Calcd for C$_{13}$H$_{22}$N$_2$Si: 235.1631[M+H]$^+$. Found: 235.1639 [M+H]$^+$. [α]$^{25}_D$−124.1 (CH$_2$Cl$_2$,c=4.9).

EXAMPLE 3

Preparation of (S)-3-(1-methylpyrrolidin-2-yl)-4-trimethylsilanyl-4H-pyridine-1-carboxylic acid dimethylamide (iii)

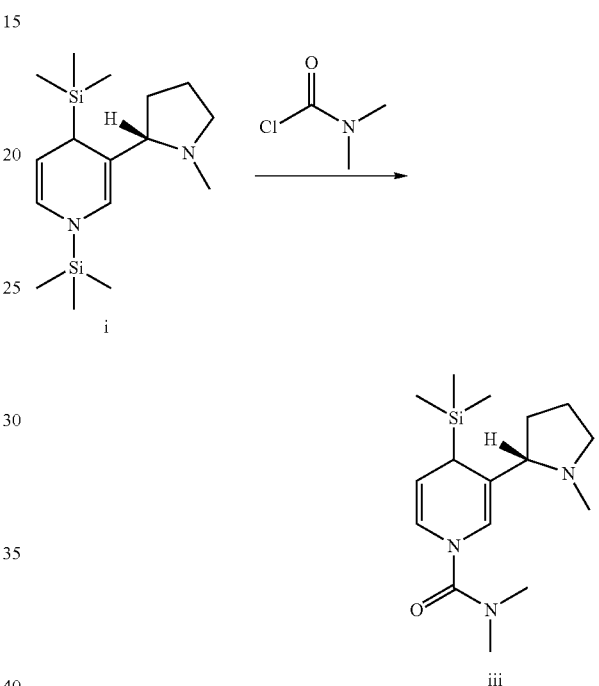

To a stirred solution of 3-(1-methylpyrrolidin-2-yl)-1,4-bis-trimethylsilanyl-1,4-dihydropyridine i (0.2 mL, 1.36 mmol) in CH$_2$Cl$_2$ (6 mL) under Ar was added dropwise dimethylcarbamyl chloride (0.19 mL, 2.04 mmol). The reaction mixture was stirred at RT for 1 day. It was then poured into a saturated solution of NaHCO$_3$ (3 mL). The aqueous phase was extracted with CH$_2$Cl$_2$ (5 times). The combined organic layers were washed with water and brine and dried over MgSO$_4$. Evaporation of the solvent under reduced pressure afforded 0.49 g of crude material that was purified by RPLC (silica gel, 5% EtOAc/hex) to give 59% (0.2506 g) of 3-(1-methylpyrrolidin-2-yl)-4-trimethylsilanyl-4H-pyridine-1-carboxylic acid dimethylamide iii as a clear oil. IR (thin film, neat, NaCl): 3363, 2924, 2348, 1657, 1449, 1377 cm$^{-1}$; $^1$H NMR (300 MHz, CDCl$_3$) δ 6.65 (d, 1 H, J=6.9 Hz), 6.35 (s 1 H), 4.83–4.78 (m, 1 H), 3.14–3.09 (m, 1 H), 2.88 (s, 6 H), 2.80–1.25 (m, 13 H), 0.085 (s, 6 H); $^{13}$C NMR (100 MHz, CDCl$_3$): δ 149.29, 147.15, 128.04, 124.49, 120.09, 106.29, 68.23, 57.35, 41.47, 38.53, 33.04, 30.34, 29.91, 22.37, 0.63, −2.00. HRMS Calcd for C$_{16}$H$_{29}$N$_3$OSi: 308.2157 [M+H]$^+$. Found: 308.2157 [M+H]$^+$. [α]$^{25}_D$−15.17 (CH$_2$Cl$_2$, c=0.145).

EXAMPLE 4

Preparation of (S)-3-benzyl-5-(1-methylpyrrolidin-2-yl)-pyridine iv

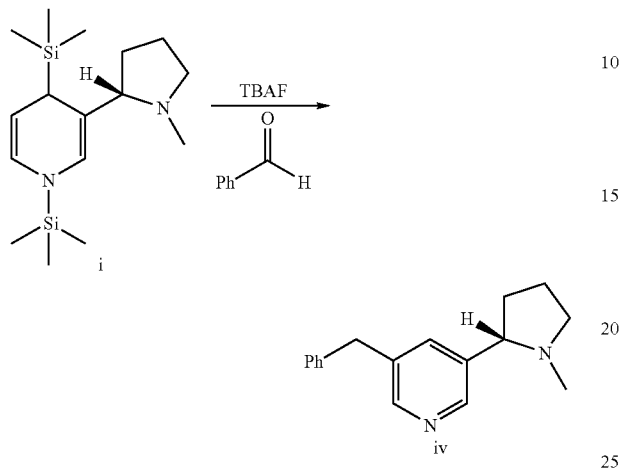

To a stirred solution of benzaldehyde (0.07 mL, 0.75 mmol) in freshly distilled THF was added dropwise 3-(1-methylpyrrolidin-2-yl)-1,4-bis-trimethylsilanyl-1,4-dihydropyridine i (0.21 g, 0.68 mmol). A degassed solution of TBAF in THF (1 M) stored over molecular sieves was slowly added to the mixture. The reaction mixture was stirred under Ar at RT for one day. It was then poured into a saturated aqueous solution of NaHCO$_3$. The product was extracted with diethyl ether (2 times). The combined organic layers were washed with brine and dried over MgSO$_4$. The solvent was evaporated under reduced pressure and the residue was purified by RPLC (silica gel, 10% MeOH/EtOAc) to give 31% (0.0525 g) of (S)-3-benzyl-5-(1-methylpyrrolidin-2-yl)-pyridine iv as a clear oil. IR (thin film, neat, NaCl): 3236, 2954, 2778, 1666, 1613, 1449, 1037 cm$^{-1}$. $^1$H NMR (400 MHz, CDCl$_3$) δ 8.40–8.34 (m, 2 H), 7.88 (dd, 1 H, J=1.6 and 13.2 Hz), 7.37–7.24 (m, 4 H), 5.84 (s, 1 H), 3.13–3.02 (m, 2 H), 2.25–1.69 (m, 10 H); $^{13}$C NMR (75 MHz, CDCl$_3$) δ 148.43, 147.42, 143.90, 140.11, 138.19, 133.30, 133.25, 128.82, 127.95, 126.81, 74.24, 74.03, 69.15, 57.04, 40.47, 35.10, 22.51. HRMS Calcd for C$_{17}$H$_{20}$N$_2$: 252.1626 [M+H]$^+$. Found: 252.1635 [M+H]$^+$. [α]$^{25}_D$ −26 (CH$_2$Cl$_2$, c=1.51).

EXAMPLES 5–9

Preparation of (S)-(−)-5-ethenyl-3-(1-methyl-2-pyrrolidinyl)pyridine maleate VI (SIB-1508Y)

These examples show the preparation of a compound, SIB-1508, by methods and intermediates of the present invention. Note that compound I is the same as compound i in examples 1–4 above, but that compounds II–IV herein are different structures than those assigned compound numbers ii–iv in Examples 1–4 above.

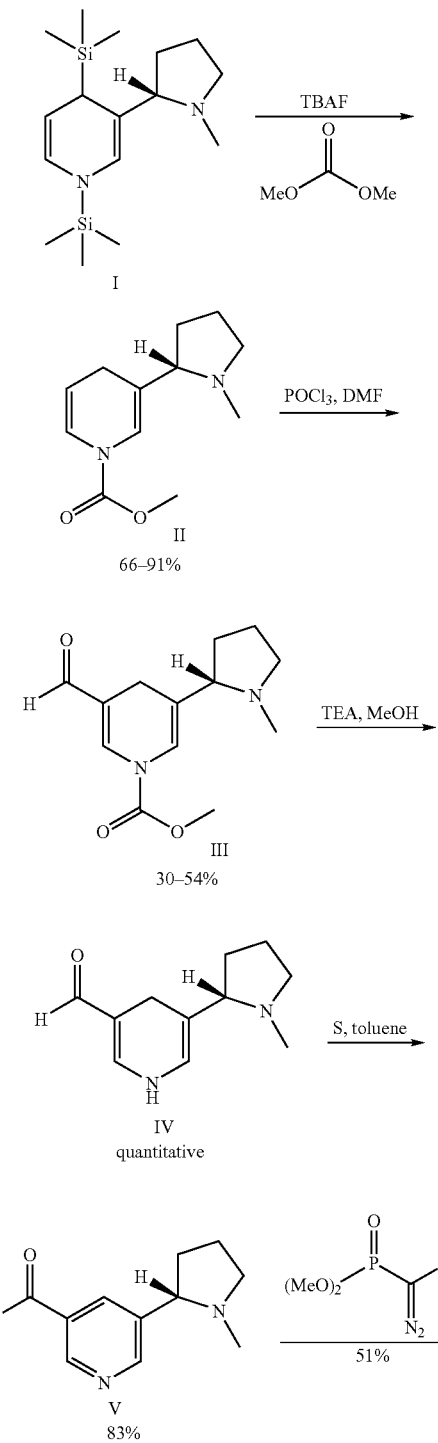

EXAMPLE 5

Preparation of (S)-3-(1-Methylpyrrolidin-2-yl)-4H-pyridine-1-carboxylic acid methyl ester II

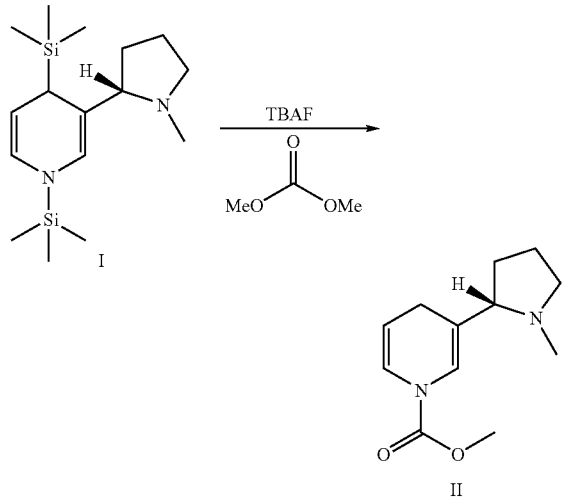

To a solution of dimethyl carbonate (0.05 mL, 0.6 mmol) in 2 mL of dry THF was slowly added 3-(1-methylpyrrolidin-2-yl)-1,4-bis-trimethylsilanyl-1,4-dihydropyridine I (0.2 mL, 0.68 mmol). A solution of TBAF in THF (0.06 mL, 0.06 mmol) was then introduced dropwise and the reaction mixture was stirred at RT for 1 h. The reaction was quenched with a saturated aqueous solution of NaHCO$_3$. The aqueous layer was extracted with ether (2 times), and the combined organic layers were washed with brine and dried over K$_2$CO$_3$. The solvent was removed under reduced pressure and the crude material was purified by RPLC (hexanes) to afford 0.1374 g (91%) of 3-(1-methylpyrrolidin-2-yl)-4H-pyridine-1-carboxylic acid methyl ester II as a clear oil. IR (thin film, neat, NaCl): 2949, 2826, 2764, 1721, 1695, 1437, 1334, 1313, 1194, 983 cm$^{-1}$. $^1$H NMR (300 MHz, CDCl$_3$): δ 6.68–6.51 (m, 2 H), 4.88–4.77 (m, 1 H), 3.65 (s, 3 H), 2.95–2.91 (m, 1 H), 2.64–2.62 (m, 2 H), 2.41–2.33 (m,1 H), 2.05–1.93 (m, 5 H), 1.68–1.53 (m, 4 H); $^{13}$C NMR (CDCl$_3$, 75 MHz) δ 151.81, 123.15, 122.74, 120.28, 119.63, 118.08, 117.71, 106.22, 105.94, 70.37, 56.60, 53.05, 40.16, 40.08, 28.76, 28.38, 22.37, 21.56, 21.05. HRMS Calcd for C$_{12}$H$_{18}$N$_2$O$_2$: 223.1447 [M+H]$^+$. Found: 223.1434 [M+H]$^+$. [α]$^{24}_D$ −65.5 (c=8, CH$_2$Cl$_2$).

EXAMPLE 6

Preparation of (S)-3-formyl-5-(1-methylpyrrolidin-2-yl)-4H-pyridine-1-carboxylic acid methyl ester (III)

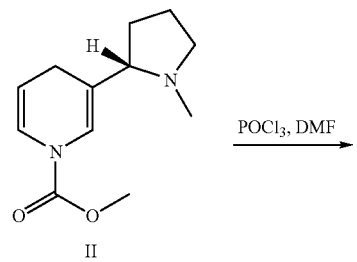

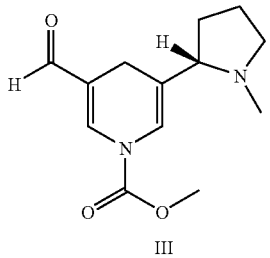

To a solution of DMF (0.04 mL, 0.54 mmol) in 4 mL of CH$_2$Cl$_2$ cooled at 0° C. was slowly added POCl$_3$ (0.025 mL, 0.27 mmol). The ice bath was removed and the mixture was stirred at RT for 30 min. It was then transferred via a double tipped needle to a solution of 3-(1-methyl-pyrrolidin-2-yl)-4H-pyridine-1-carboxylic acid methyl ester II (0.0404 g, 0.18 mmol) in 4 mL of CH$_2$Cl$_2$ cooled at 0° C. The reaction mixture was stirred at RT for 1 day. A solution of NaOAc (0.024 g, 0.29 mmol) in 0.5 mL of water was added and the reaction mixture was stirred at RT for 20 min. A saturated aqueous solution of NaHCO$_3$ was slowly added until pH was basic (about 10 mL). The aqueous layer was extracted with CH$_2$Cl$_2$ (4 times), and the combined organic layers were dried over MgSO$_4$. After evaporation of the solvent under reduced pressure, the crude material was purified by RPLC (15% EtOAc/hexanes) to afford 0.0241 g (54%) of (S)-3-formyl-5-(1-methylpyrrolidin-2-yl)-4H-pyridine-1carboxylic acid methyl ester III as white crystals, mp 78–80° C. IR (thin film, neat, NaCl): 2955, 2767, 1731, 1667, 1620, 1437, 1394, 1203, 991 cm$^{-1}$; $^1$H NMR (CDCl$_3$, 300 MHz) δ 9.45 (s, 1 H), 7.65 (m, 1 H), 6.81 (s, 1 H), 3.91 (s, 3 H), 3.12–3.07 (m, 1 H), 2.93 (s, 2 H), 2.59 (m, 1 H), 2.20–2.12 (m, 3 H), 1.81–1.62 (m, 5 H); $^{13}$C NMR (CDCl$_3$, 75 MHz) δ 191.13, 141.44, 122.61, 120.52, 118.42, 69.75, 56.98, 54.47, 40.61, 29.45, 22.91, 19.86. HRMS Calcd for C$_{13}$H$_{18}$N$_2$O$_3$: 251.1396 [M+H]$^+$. Found: 251.1390 [M+H]$^+$. [α]$^{25}_D$ −5.17 (c=0.8, CH$_2$Cl$_2$).

EXAMPLE 7

Preparation of (S)-5-(1-methylpyrrolidin-2-yl)-1,4-dihydropyridine-3-carbaldehyde (IV)

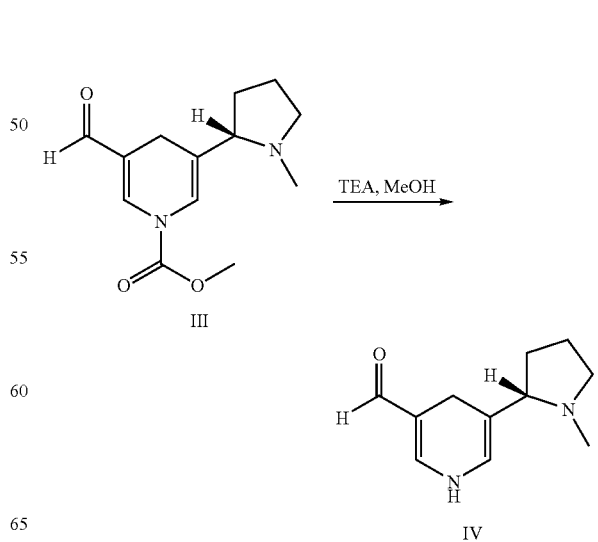

To a solution of (S)-3-formyl-5-(1-methyl-pyrrolidin-2-yl)-4H-pyridine-1-carboxylic acid methyl ester III (0.0124 g, 0.05 mmol) in 2 mL of anhydrous MeOH was slowly added triethylamine (0.02 mL, 0.15 mmol), and the reaction mixture was stirred at RT for 1 day. Evaporation of the solvent afforded a quantitative yield (0.010 g) of (S)-5-(1-methyl-pyrrolidin-2-yl)-1,4-dihydro-pyridine-3-carbaldehyde IV as a yellow oil. The product was used without further purification. IR (thin film, neat, NaCl): 3416–3244, 2957, 1595, 1509, 1377, 1228 cm$^{-1}$. $^1$H NMR (CDCl$_3$, 300 MHz) δ 9.14 (s, 1 H), 6.85 (d, 1 H, J=6 Hz), 648 (s, 1 H), 6.00–5.99 (m, 1 H), 3.05–3.00 (m, 3 H), 2.45 (m, 1 H), 2.19–2.11 (m, 4 H), 1.83–1.67 (m, 4 H); $^{13}$C NMR (CDCl$_3$, 75 MHz) δ 189.59, 146.95, 119.91, 119.01, 112.67, 70.03, 57.03, 40.69, 28.96, 22.80, 20.37. HRMS Calcd for C$_{11}$H$_{16}$N$_2$O: 193.1341 [M+H]$^+$. Found: 193.1334 [M+H]$^+$. [α]$^{28}_D$–80.7 (c=0.55, CH$_2$Cl$_2$).

EXAMPLE 8

Preparation of (S)-5-(1-methylpyrrolidin-2-yl)pyridine-3-carbaldehyde (V)

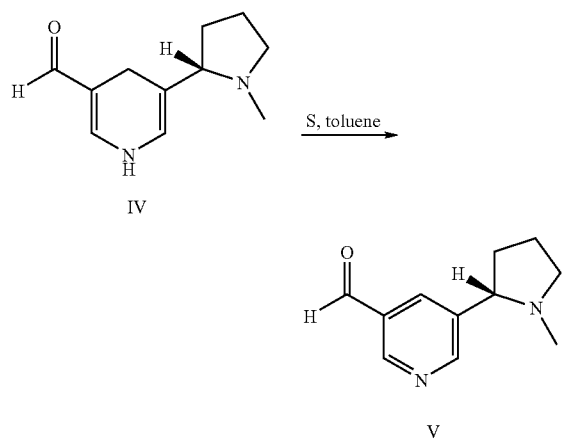

A solution of (S)-5-(1-methylpyrrolidin-2-yl)-1,4-dihydropyridine-3-carbaldehyde IV (0.011 g, 0.044 mmol) and elemental sulfur (0.0015 g, 0.044 mmol) in 2 mL of toluene was refluxed for 1 day. After filtration through a pad of Celite, and evaporation of the solvent under reduced pressure, the crude material was purified by RPLC (silica gel, 5% EtOAc/hexanes then EtOAc) to afford 0.007 g (83%) of 5-(1-methylpyrrolidin-2-yl)pyridine-3-carbaldehyde V as a clear oil. IR (thin film, neat, NaCl): 2950, 1586, 1370, 1120 cm$^{-1}$. $^1$H NMR (CDCl$_3$, 300 MHz) δ 10.13–10.12 (m, 1 H), 8.97–8.96 (m, 1 H), 8.79 (s, 1 H), 8.18 (s, 1 H), 3.30–3.20 (m, 2 H), 2.38–1.67 (m, 4 H); $^{13}$C NMR (CDCl$_3$, 100 MHz) δ 191.26, 154.81, 150.91, 135.13, 131.69, 68.53, 57.19, 40.64, 40.64, 35.66, 23.02. HRMS Calcd for C$_{11}$H$_{14}$N$_2$O: 191.1184 [M+H]$^+$. Found: 191.1182 [M+H]$^+$. [α]$^{23}_D$–92 (c=0.2, CH$_2$Cl$_2$).

EXAMPLE 9

Revised Preparation of (S)-3-ethynyl-5-(1-methylpyrrolidin-2-yl) pyridine or SIB-1508Y (VI)

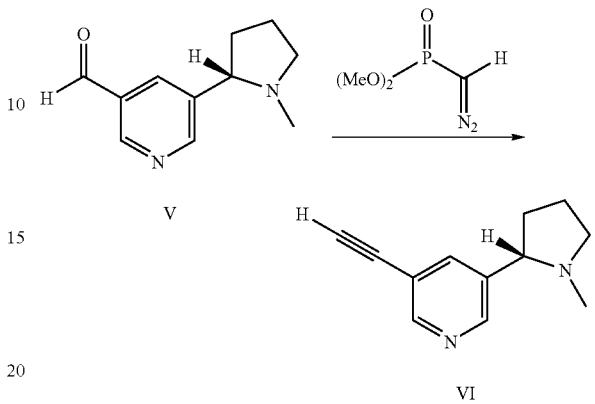

To a solution of tBuOK in THF (0.08 mL, 0.08 mmol) cooled at −78° C. was added dropwise a solution of methyl diazomethyl phosphonate in THF (0.1 mL, 0.08 mmol). The solution was stirred at −78° C. for 5 min, then a solution of 5-(1-methylpyrrolidin-2-yl)pyridine-3(V) (0.0126 g, 0.066 mmol) in THF (1 mL) was added via a double tipped needle. The reaction mixture was stirred at −78° C. for 16 h then allowed to warm to RT over 2 h. After evaporation of the solvent under reduced pressure, the crude material was purified by RPLC (silica gel, 10% EtOAC/hexanes) to afford 0.0061 g (51%) of 3-ethynyl-5-(1-methylpyrrolidin-2-yl)-pyridine (VI) as a clear oil. The data were identical to those described in the literature (Bleicher, L. S.; Cosford, N. P. D.; Herbault, A.; McCallum, J. S.; McDonald, I. A. *J. Org. Chem.* 1998, 63, 1109).

The foregoing is illustrative of the present invention, and is not to be construed as limiting thereof. The invention is defined by the following claims, with equivalents of the claims to be included therein.

That which is claimed is:

1. A compound selected from the group consisting of compounds of Formula II, Formula III, Formula IV, and Formula V:

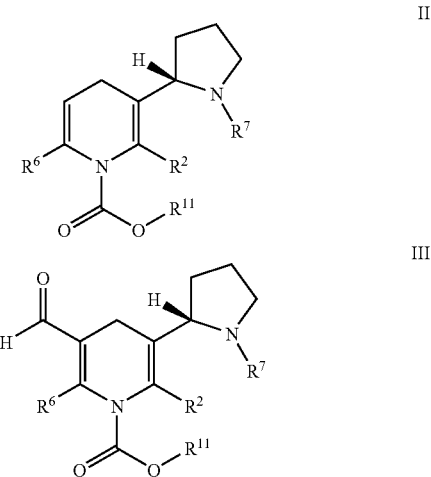

-continued

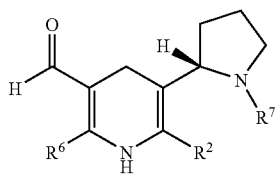
IV

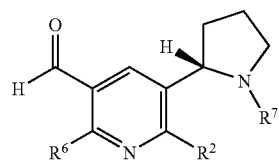
V wherein:
R² and R⁶ are each independently selected from the group consisting of H, alkyl, aryl, alkenyl, alkynyl, alkoxy, and halo,
R⁷ is selected from the group consisting of consisting of H and alkyl; and
R¹¹ is selected from the group consisting of alkyl and aryl.

2. A compound of claim 1, wherein said compound is a compound of Formula II.

3. A compound of claim 1, wherein said compound is a compound of Formula III.

4. A compound of claim 1, wherein said compound is a compound of Formula IV.

5. A compound of claim 1, wherein said compound is a compound of Formula V.

* * * * *